(12) United States Patent  (10) Patent No.: US 8,569,935 B1
Kosierkiewicz  (45) Date of Patent: Oct. 29, 2013

(54) PIEZOELECTRIC SHOE INSERT

(76) Inventor: Tomasz Andrzej Kosierkiewicz, Mount Vernon, IL (US)

(*) Notice: Subject to any disclaimer, the term of this patent is extended or adjusted under 35 U.S.C. 154(b) by 262 days.

(21) Appl. No.: 13/020,392

(22) Filed: Feb. 3, 2011

Related U.S. Application Data

(63) Continuation-in-part of application No. 12/835,972, filed on Jul. 14, 2010, now abandoned, and a continuation-in-part of application No. 12/559,061, filed on Sep. 14, 2009, now abandoned.

(60) Provisional application No. 61/347,963, filed on May 25, 2010.

(51) Int. Cl.
H01L 41/047 (2006.01)
H01L 41/113 (2006.01)

(52) U.S. Cl.
USPC .......................... 310/363; 310/339

(58) Field of Classification Search
USPC .................. 310/300, 339, 363, 364, 800
See application file for complete search history.

(56) References Cited

U.S. PATENT DOCUMENTS

| | | | | |
|---|---|---|---|---|
| 3,941,137 A * | 3/1976 | Vredenbregt et al. | ........... | 607/49 |
| 5,824,033 A * | 10/1998 | Ferrari | ........... | 607/142 |
| 2003/0067245 A1* | 4/2003 | Pelrine et al. | ........... | 310/311 |
| 2004/0173220 A1* | 9/2004 | Harry et al. | ........... | 128/892 |
| 2007/0141473 A1* | 6/2007 | Yang et al. | ........... | 429/303 |
| 2008/0083139 A1* | 4/2008 | Mullen | ........... | 36/136 |
| 2008/0108889 A1* | 5/2008 | Lin et al. | ........... | 600/372 |
| 2009/0154053 A1* | 6/2009 | Biggs et al. | ........... | 361/272 |
| 2010/0109486 A1* | 5/2010 | Polyakov et al. | ........... | 310/365 |
| 2011/0131838 A1* | 6/2011 | Pas et al. | ........... | 36/140 |

* cited by examiner

Primary Examiner — Thomas Dougherty
(74) Attorney, Agent, or Firm — Jessica W. Smith

(57) ABSTRACT

An electrical generating device for use with a shoe worn by a user may include a shoe insert to be positioned within the shoe, and the shoe insert may include an elastomer electrode to apply an electrical signal to the user. The elastomer electrode may include a metal integral conductive silicon rubber conductive surface. The elastomer electrode may include silver, silver plated copper, or conductive metal plated material filled silicon filled silicon sheet or a conductive adhesive gel layer. The elastomer electrode may include a conductive carbon film or a conductive metal sheet. The elastomer electrode may include a conductive silver sheet or may include a conductive metal sheet.

18 Claims, 11 Drawing Sheets

PIEZOELECTRIC SHOE INSERT

PRIORITY

The present application claims priority under 35 USC section 119 based upon a provisional application with a Ser. No. 61/347, 963 which was filed on May 25, 2010.

RELATED APPLICATIONS

The present U.S. Utility Patent Application claims priority pursuant to 35 U.S.C. §120, as a continuation in part, to U.S. Utility patent application Ser. No. 12/559,061 having a filing date of Sep. 14, 2009 now abandoned.

The present U.S. Utility Patent Application claims priority pursuant to 35 U.S.C. §120, as a continuation in part, to U.S. Utility patent application Ser. No. 12/835,972 having a filing date of Jul. 14, 2010 now abandoned.

FIELD OF THE INVENTION

The present invention relates to a shoe or shoe insert, which may include an impact-sensing element made from piezoelectric material. In particular it relates to a non-adhesive medical electrode.

BACKGROUND

Piezoelectric materials are used in many applications for actuation, sensing, and electric energy harvesting. Piezoelectricity is the ability of crystals to generate a voltage in response to applied mechanical stress. As such, a mechanical stress applied on a piezoelectric material creates an electric charge. Piezoceramics will give off an electric pulse even when the applied pressure is as small as sound pressure. This phenomenon is called the direct piezoelectric effect and is used in sensor applications such as microphones, undersea sound detecting devices, pressure transducers, and electric energy harvesting to power other electronic devices. Piezoelectric materials can also function quite opposite in the converse piezoelectric effect, in which an electric field applied to a piezoelectric material changes the shape of the material as a result of the applied electric energy. In contrast to the direct piezoelectric effect, the converse piezoelectric effect only causes an elongation/contraction of the dipoles in the material causing the entire material to elongate/contract, and does not produce electrical charges. The converse piezoelectric effect makes possible piezoelectric actuators for precision positioning with high accuracy.

Early attempts to suppress organic pain and other neurophysical effects utilizing electrical stimulation occurred as early as about 2,000 years ago when it was discovered that gout apparently could be successfully treated by placing the diseased extremities in a tub of water filled with electric eels. Later, headaches were treated using a similar approach. A detailed, scientific investigation was finally conducted by Professor Galvani of the University of Bologna, which investigation is credited with ultimately leading to the development in the 1800's of electrical equipment for suppression of organic pain.

In 1967, a Dr. Sweet at Massachusetts General Hospital developed the first Transcutaneous electrical nerve stimulation—T.E.N.S. unit. The effectiveness of T.E.N.S. therapy is based on its incorporating two major pain control theories. Under the so-called Gate Control Theory, pain can be inhibited and suppressed by "closing the gate" on pain signals, as such signals arrive at Central Nervous System centers. This theory postulates that by providing electrical stimulation of a sufficiently high amplitude, the electrical signals race up large myelinated fibers faster than the pain signals travel up smaller myelinated or unmyelinated fibers. The neutral impulses transmitting pain information to the brain thus become interrupted, and since the brain fails to receive the pain signals, no pain is perceived. The other theory incorporated in T.E.N.S. units is the Endorphin Theory, also known as the Endogenous Opiate Theory. This theory postulates that the sustained input of T.E.N.S. signals triggers the release of naturally occurring pain making endorphins and enkephalins (morphine-like substances). These natural substances seemingly block pain signals by a mechanism similar to conventional drug therapy, and inhibit pain information from reaching the brain.

T.E.N.S. therapy is based on a non-invasive, non-narcotic concept of pain management, which is non-addictive, is not subject to abuse, and does not interact with drugs.

T.E.N.S. therapy has already proven to be an effective modality in treating the organic pain problems associated with the following conditions: chronic lumbar and cervical strains or sprains, degenerative disc disease, degenerative arthritic disease, neuropathies, neuralgias, post-lumbar laminectomy syndrome, post-thoracotomy syndrome, bursitis, post phlebitis syndrome, phantom limb syndrome, and tension and migraine headaches.

There are many causes of painful sensory neuropathy. In one subtype referred to as "small-fiber painful sensory neuropathy", only the A delta (small myelinated) and nociceptive C (unmyelinated) nerve fibers are affected. Studies indicate that this condition represent the most common type of painful sensory neuropathy in patients older than 50 years of age. It is vastly under recognized, and in most cases, no cause can be found. In another group of neuropathies associated with pain, the discomfort has caused in part by damage to small nerve fibers, but large nerve fibers (A beta and A gamma nerve fibers) that are responsible for proprioception, vibratory sensation, muscle-stretch reflexes, and muscle strength are also affected. The distinction between the two subtype painful sensory neuropathies is not trivial, since the underlying cause is most likely to be unidentifiable when both large and small fibers are affected. Irrespective of the subtype of neuropathy, the pain generated by damage to small nerve fibers is debilitating and responds poorly to treatment. Finding and treating the cause is the best long-term strategy, but it is not routinely possible, and even when it is possible, treatment may not be able to relieve pain for many months or longer.

Typical symptoms of neuropathic pain related to small fibers including burning (the sensation that the feet are on fire), sharp pain (described as a knife like jabbing, or pins and needles), shooting pain and aching in the toes and feet (reflecting damage to the longest axons). Pain emanating from the peripheral nerves indicated by the description of the feet as tingling, numb, or feeling tight, wooden, or dead. Peripheral nerve pain if often exacerbated at night, but some patients described pressure-induced pain with standing or walking.

Another cause may include plantar fascitis, arthritis, bursitis, tendonitis, polymyalgia rheumatica, and lumbosacral radiculopathies (with or without spinal stenosis).

The pain in the toes, related to entrapment of the posterior tibial nerve in tarsal tunnel (space beneath the flexor retinaculum and behind the medial malleolus) may mimic painful sensory neuropathy.

Pain can occur without provocation (be stimulus-independent as with burning and paraesthesias accompanying small fiber neuropathies) or can be stimulus evolved (for example, hyperalgesia in response to noxious stimuli or allodynia induced by non-noxious stimuli). The cause of nerve damage does not dictate the type of pain, and non-specific therapies that are effective for one should also be applicable to others.

Summary of Clinical Trials:

Antidepressant aid drugs, 1. Tricyclic antidepressants. i. Amitriptyline. ii. Nortriptyline. iii. Desipramine.

2. Selective Serotonin Reuptake Inhibitors, SSRI.

i. Paroxetine. ii. Citalopram.

Other antidepressants, ii. Venlafaxine. ii. Bupropion.

Anticonvulsants: 1. Carbamazepine. 2. Phenytoin. 3. Gabapentin.

4. Oxcarbazepine. 5. Lamotrigine. 6. Clonazepam. 7. Topiramate. 8. Pregabalin.

Antiarrhythmic drugs: mexiletine.

Non-narcotic analgesics: Tramadol.

Narcotic analgesics, 1. Oxycodone. 2. Morphine.

Topical anesthetics: 1.5% Lidocaine patch, 2. Capsaicin, 3. NMDA (N-methyl-D-aspartate Glutamate antagonists) Dextromethorphan.

At best, current therapies for painful sensory neuropathy result in 30 to 50% reduction in pain and such a reduction rarely meets patients' expectation.

It remains uncertain whether adequate pain relief can be achieved with a multidrug strategy particularly with the use of pharmacological agents targeted at more than one side in a pain pathway.

At the present time, there are no guidelines available from professional organizations for a treatment of painful sensory neuropathy. (1)

Diabetic neuropathy is a common complication of diabetes. Usually progresses, gradually involves small and large sensory fibers. Symptoms such as loss of ability to sense pain, loss of temperature sensation, and developing neuropathic pain "glove and stocking" distribution, beginning in the lower limbs, first affecting the toes and then progressing upward.

Symptoms of neuropathic pain are commonly reported in patients with the diabetic neuropathy. In one study, 7-13% of the patients had pain and paresthesia when they were diagnosed as having type II diabetes mellitus. The prevalence of pain and paresthesia were 20% and 33% 10 years after diagnosis. (2)

Diabetes was the sixth leading cause of death in the US in 2002. Between 1990 and 2000, number of people in the US diagnosed with diabetes increased by 49%. An estimated 18.2 million Americans now suffered with the disease, with 13 million diagnosed and 5.2 million undiagnosed. If the diabetes prevalence rate were to remain at current levels, the census bureau estimates the number of people diagnosed with diabetes would increase to nearly 14.5 million by 2010 and 17.4 million by 2020.

Diabetic neuropathy is one of the most common, long term complication of diabetes mellitus. Diabetic neuropathy has the highest morbidity and mortality rate and it is associated with a substantial reduction in quality of life. Approximately 20% of patients have neuropathy at the time of diabetes diagnosis, and the number increases to as much as 50% of patients who have had diabetes for 15 or more years.

The patients diagnosed with diabetes and diabetic neuropathy had significant differences in total medical costs. The patient with diabetic neuropathy cohorts had significantly higher mean total medical costs than diabetes mellitus patient ($24,765 versus $4819). This increase in cost associated with diagnosis of neuropathy included all cost component: Inpatient ($7282 versus $1005), outpatient ($14,137 versus $2548), emergency room ($889 versus $178), and a pharmaceutical ($6526 versus $1098) costs. The patient diagnosed with diabetes had a mean total diabetes related medical cost of $1297; however, with the addition of neuropathy complication the mean total diabetes related cost with significant increase to $5125 for the diabetic neuropathy patient. (3)

Peripheral neuropathy is one of the most common complications of both type 1 and type 2 diabetes. In a population-based study, 22% of the diabetic cohort had peripheral neuropathy that was moderate to severe. Long standing peripheral neuropathic pain associated with peripheral neuropathy occurs in one of six diabetic subjects. When symptoms are present, they may be negative or positive. Negative symptoms include loss of sensation and loss of strength, while positive symptoms include pricking or pain. One of the most distressing symptoms that people can suffer from is neuropathic pain and paresthesia. Chronic painful peripheral neuropathy is common and often severe, but frequently unreported and inadequately treated. (4)

Diabetes mellitus is one of the most common chronic medical condition affecting over 100 million people worldwide of whom up to 60% may develop diabetic polyneuropathy.

The pain transmission via the axons, which is manifested as either a small myelinated (A delta) or thinner unmyelinated (C) fibers each performing specific tasks. Somatic pain arises from the skin, muscles, or joints and can be classed as either superficial or deep. Superficial pain is often sharp or pricking sensation and is transmitted along the fine lightly myelinated A delta fibers. Alternatively, deep somatic pain, often a burning, itching, or aching type of pain with longer duration arising from the deep layers of soft tissue or joint. In normal condition, this form of pain almost always indicates tissue damage and is conducting along the slower unmyelinated C-fibers. (5)

The main advantage of TENS system is its portable nature as a topical application of low-frequency currents making it safe. TENS machines are clearly contraindicated in patients with pacemakers. (5)

A trial conducted by Meyler (6) evaluated the use of TENS in 200 patients with a variety of pain syndromes. The results demonstrated that 53% with peripheral nerve damage reported pain reduction.

Neuropathic pain is characterized by abnormal stimulus-evoked pain, which is usually described as hypersensitivity. It can result from injuries to the peripheral sensory nerve. Hypersensitivity is defined as a condition of extreme discomfort or irritability in response to normally non-noxious tactile stimulation. Neuropathic pain (hypersensitivity) can be subdivided into hyperalgesia and allodynia. The International Association for the Study of Pain (IASP) define hyperalgesia as a greater than normal pain response to painful stimuli, and the term allodynia refers to pain produced by a normally non-painful stimulus.(7)

In the clinical settings, Transcutaneous Electrical Nerve Stimulation (TENS) is one of the commonest treatments for hypersensitivity. (7)

Between 80-85% of patients experienced beneficial effect of electrotherapy for neuropathic pain. Combination of therapy with amitriptyline and electrotherapy appears to be superior to either drug or electrotherapy alone.

Because symptoms would recur when electrotherapy discontinued, it appears a maintenance treatment protocol should be developed for each patient. TENS device generated a biphasic, exponentially decaying waveforms with pulse. (8)

There is some suggestion that the TENS may have an effect for central post-stroke pain, visuo-spatial neglect, and neglect-related postural instability. Transcutaneous electric nerve stimulation may have a possible use as a sensory stimulus to rehabilitate sensory function or as a sensory prosthesis to boost sensory perception and subsequent functional activity. (9)

1. Painful sensory neuropathy Jerry R. Mendell, M.D and Varise Sahenk, M.D, PhD. New England Journal of Medicine 348; 13-Mar. 27, 2003.
2. Effects of Treatments for Symptomatic and Painful Diabetic Neuropathy:
Systemic review by Man-Chun Wong, Joanne W, Y. Chung, and Thomas S. Wong B M J 2007; 335; 87 originally published on Jun. 11, 2007.
3. Resource use among patients with diabetes, diabetic neuropathy, and diabetes with depression by Trong K. Le, Stephe N. Able, and Maureen J. Lage. Cost Effectiveness and Resource Allocation 2006, 4:18 published on Feb. 23, 2006.
4. The Prevalence, Severity, and Impact of Painful Diabetic Peripheral Neuropathy in Type 2 Diabetes by Mark Davies, MSC, Sinead Brophy, Ph.D., Rhys William Ph.D., and Ann Taylor, MSC from diabetes care, Volume 29, #7, July 2006.
5. The Pathogenesis and Management of Painful Diabetic Neuropathy: A Review by M. C. Spruce, J. Potter, and D. V. Coppini. Diabetic Medicine, 20, 88-98 in 2003.
6. Meyler W J, De Jongste M J, and Rolf C clinical evaluation of pain and treatment with electrostimulation: A study of TENS in patient with different pain syndrome. Clinical Journal of Pain in 1994: 10:22-27,
7. Transcutaneous Electrical Nerve Stimulation for Neuropathic pain by G. L. Y. Cheing and M. L. M. Luk Journal of Hand Surgery (British and European volume, 2005) 30B, column 1, column 50-55.
8. Transcutaneous electrostimulation: Emerging Treatment for Diabetic Neuropathy Pain by Michael Alvero, DPM, Dinesh Kumar, M.D., and
Inderjeet S. Julka, M.D. Diabetes Technology and Therapeutics Volume#1, 1999, pages 77 to 81.
9. Use of Transcutaneous Nerve Stimulation to Treat Sensory Loss After Stroke by Sarah Tyson from Physiotherapy Research International, 8 (1) 53-57, 2003.

As discussed above, it has been proven that electrical energy can have therapeutic effect on human or animal tissue, muscles, and other physiological areas. There are a variety of methods and devices on the market that use this technique. For example, what is known as a TENS unit or device converts electrical energy from an external alternating current (AC) source or a battery into an electrical field that is applied to an injured or targeted portion of the body.

One problem with known devices and systems is they require an external or battery electrical power source. This usually means either limited mobility during treatment or added weight and bulk, which can be counterproductive or cumbersome for the user. Furthermore, most devices, including TENS devices, require electrodes to be adhesively placed on a targeted location of the body. Most times, the electrodes then must be hard-wired to a control unit. This is cumbersome to install and wear. It requires immobilization of the user to place the electrodes or remove them.

Many existing devices are also relatively expensive, and require close monitoring or even operation by health care professionals.

There is a real need in this area for improvement. For example, there is a real need for technology that utilizes the benefits of electrical fields for therapeutic purposes, but with less constrictions on mobility of the user during treatment. There is also a need for a more efficient and economical method for administering such therapy.

SUMMARY

An electrical generating device for use with a shoe worn by a user may include a shoe insert to be positioned within the shoe, and the shoe insert may include an elastomer electrode to apply an electrical signal to the user.

The elastomer electrode may include a metal integral conductive silicon rubber conductive surface.

The elastomer electrode may include a silver plated copper filled silicon sheet or a conductive adhesive gel layer.

The elastomer electrode may include a conductive carbon film or a conductive metal sheet.

The elastomer electrode may include a conductive silver sheet or may include a conductive metal sheet.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

Figure 1:
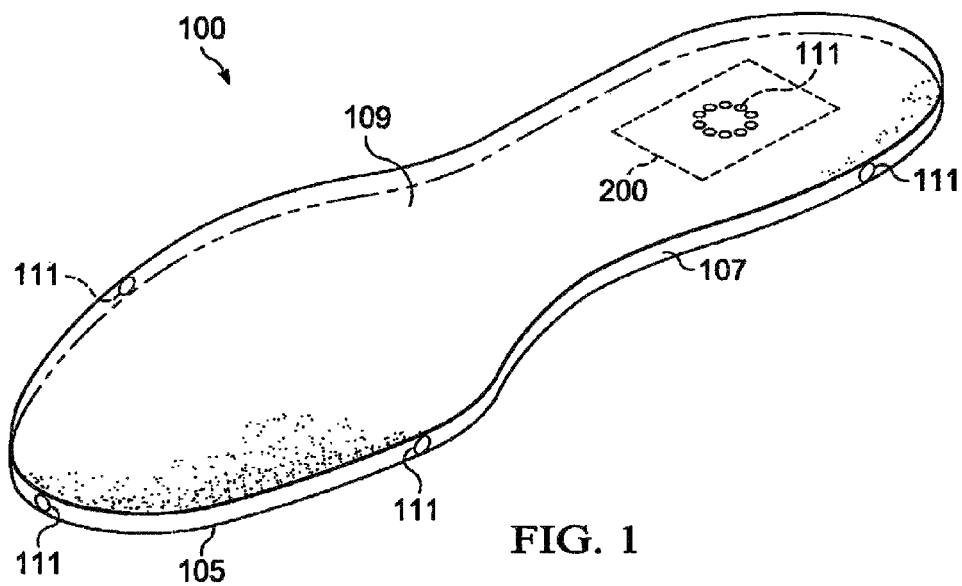
FIG. 1 illustrates a perspective view of a shoe insert of the present invention.

The present invention may relate to a product, in particular a shoe insert, or a shoe, which may incorporate an impact-sensing element made from piezoelectric material.

Piezoelectric material may be used for scavenging energy from ambient mechanical energy in the form of a mechanical disturbance (e.g., stress, strain, vibration, shock, motion, bending, flexing, pushing, deflexion, and the like. If a mechanical disturbance is applied to piezoelectric material, electrical energy may be generated, which may be conditioned and stored in the capacitor bank or may be used instantaneously. Piezoelectric energy harvests and converts mechanical energy to electric energy by stressing a piezoelectric material. The stress in a piezoelectric material may result in a charge separation across the device producing an electric field and consequently a voltage drop proportional to stress applied. Multiple generators, energy harvesting systems preferably include advanced, high charge piezoelectric ceramic fibers (PZT, PLZT, or other electro-chemistries), rods, foils, composites, or other shapes (referred to as piezoelectric ceramic fibers).

In response to impact, (while walking or running) the piezoelectric material generates an electrical signal. This electric signal may be applied directly or indirectly to transcutaneous nerve stimulating device which may be partially molded into or contained in the product, thus causing circuitry to energize the transcutaneous nerve stimulating device for the purpose of treatment of pain, numbness, tingling, burning, hypersensitivity, hyperalgesia, allodynia, (painful peripheral neuropathy, entrapment mononeuropathy i.e.: Tarsal tunnel syndrome, or sciatic neuropathy;), central sensory loss, dysesthesia, and paresthesia, central post-stroke pain, visuo-spatial neglect, and neglect-related postural instability, (central nervous system disorders i.e. myelopathy or stroke), other causes of pain may include plantar fascitis, arthritis, bursitis, tendonitis, polymyalgia rheumatica, and lumbosacral radiculopathies, but not limited to, to include other indications where the application of electric potential would be beneficial. The transcutaneous nerve stimulating device may have a plurality of operating modes, rate modulation, amplitude modulation and strength-duration/rate modulation, and may obviate the phenomenon of accommodation, for example: biphasic burst exponentially decaying waveforms with pulse, with an optional on/off switch (wireless).

The energy generator produces energy and may include any type of generator that produces an alternating current (AC) or direct current (DC). The generator may include a piezoelectric and/or electrostrictive material of any type, shape, or size. The multiple energy generators or a single energy generator may include the same of type of generators or a combination of different types of generators. Diode bridges may include an arrangement of diodes connected as a bridge circuit providing rectification of the input voltage to provide a substantially constant polarity output voltage for any polarity of the input voltage. The diode bridges may function to control Alternating Current input into Direct Current output. The size of the diode bridges may vary depending on the particular application for which diode bridge circuit is being used. The diode bridge may include a full or half way wave bridge diode. Semiconductor diodes are preferred due to their low cost and compact design.

i. Piezoelectric material may be used as energy generator that produce Alternating Current (AC) and thus acting as transcutaneous electrical nerve stimulator (TENS).

ii. Piezoelectric material may be used as energy generator producing Alternating Current (AC) providing circuitry to energize the transcutaneous nerve stimulating device for the purpose of treatment of pain. The transcutaneous nerve stimulating device has been provided with operating modes.

iii. Piezoelectric material may be used as energy generator converting Alternating Current into Direct Current output to energize circuitry for the transcutaneous nerve stimulating device for purpose of treatment of pain (painful peripheral neuropathy) or other types of pain.

The transcutaneous nerve stimulating may be provided with selectable operating modes to stimulate the transcutaneous nerve.

iv. Piezoelectric material may be used as energy generator converting Alternating Current into Direct Current supplying battery when the battery can be used to energize circuitry of the transcutaneous nerve stimulating device.

a. Piezoelectric sensor may be used to generate a signal to a battery powered transcutaneous nerve stimulating device to stimulate the cutaneous nerve. An electrode 111 may be placed on the skin over the cutaneous nerve endings of the medial calcaneal branch of tibial nerve, medial plantar nerve, lateral plantar nerve, saphenous nerve, deep peroneal nerve, superficial peroneal nerve, sural nerve, but not limited to.

v. Piezoelectric material used as energy generator converting Alternating Current into Direct Current supplying battery when the battery can be used to energize circuitry of the photo-energy treatment (U.S. Pat. No. 6,607,550 incorporated by reference in its entirety) device.

An electrical circuit may be connected to the said piezoelectric element for collection, storage, or modification of said electrical potential connected to at least two spaced electrode means of opposite polarity for applying said electrical potential to skin surface.

The number, the size, and distance of the electrodes can be customized.

The electrical energy per pulse can be selectable to a predetermined value.

The electrical potential across the electrodes can be varied to predetermined values.

An electrical circuit may be connected to the said piezoelectric element for the collection, storage, or modification of electrical potential with an optional on/off switch for wireless control.

Electrodes are connected to the shoe insert. Where the shoe insert has electrically conductive body (sole of the foot) contact layer (electrodes) and electrically insulative composite.

Figure 12:
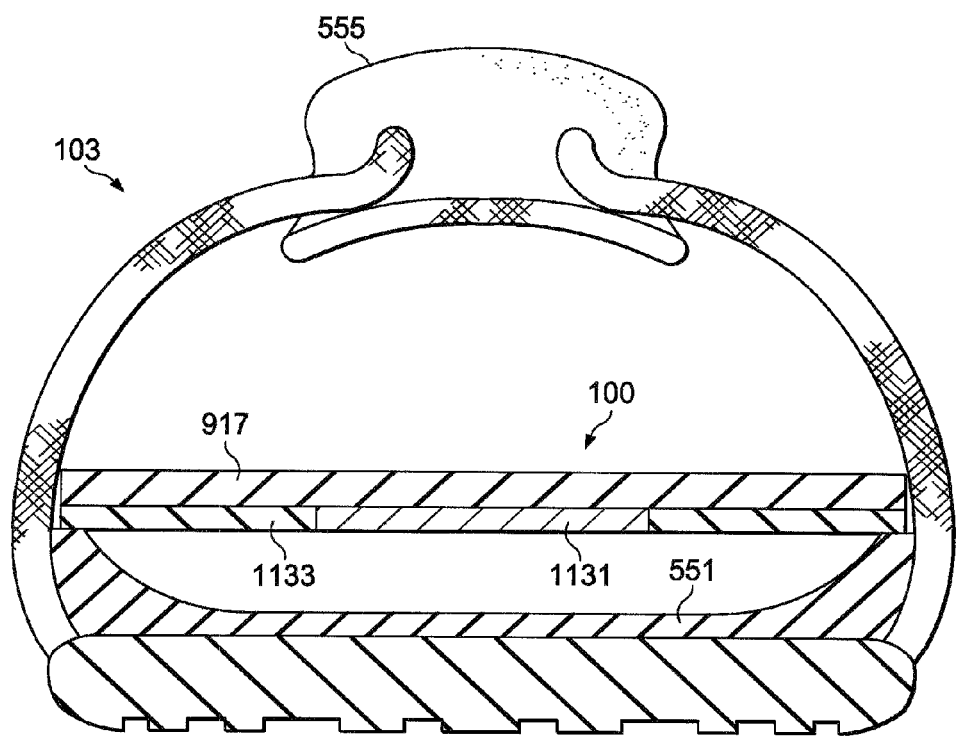
FIG. 12 illustrates a cross-sectional view of the insert of the present invention under no load and in a first position.

In one embodiment The shoe insert has elastic properties, in a neutral position it is flat and does not conform to inner surface of the molded shoe insole (see FIG. 12). When foot is introduced into the shoe, the shoe insert will then stretch to conform to the shape of the molded shoe insole (see FIG. 13). The mechanical disturbance (stress, strain, vibration, shock, motion, bending, flexing, pushing, deflexion, and the like) will activate the piezoelectric material within the shoe insert even at rest, and not necessarily only when walking and alike.

This invention is directed to the providing of a transcutaneous nerve stimulator which may take the form of a shoe insert 100 or electric generator which may generate electricity and which is designed to be utilized in T.E.N.S. (Transcutaneous Electrical Nerve Stimulation) therapy.

In response to impact, (while walking or running) an electric generator may include piezoelectric material which may generate electrical power which may be stored in a battery in order to provide battery-powered energy at a later time or the electrical power may be immediately applied to an area of to the foot for example directly to a nerve stimulating device which may be a transcutaneous nerve stimulating device which may be partially or wholly molded or contained in the product. The nerve stimulating device may generate an electrical signal to energize the transcutaneous nerve or other nerve for the purpose of treatment of pain (painful peripheral neuropathy) or other types of treatment.

The nerve stimulating device or eyelet electrodes 111 is provided having a plurality of operating modes to generate a signal which includes rate modulation, amplitude modulation and strength-duration/rate modulation, obviating the phenomenon of accommodation.

The shoe insert may have an electrically conductive surface contact layer (in contact with sole of the foot) and electrically insulating surface. (see FIGS. 7 and 10)

The energy generator produces energy and may include any type of generator that produces an alternating current (AC), including for example, piezoelectric generators, magnetic generators, and the like. The energy harvesting system may include the same type of generators or a combination of different types of generators.

The electric generators may be piezoelectric energy generators may include piezoelectric ceramic fibers, such as in piezoelectric fiber composites, piezoelectric fiber composite bimorphs, piezoelectric multilayer composites, and the like.

The electric generators may be multiple kinds of generators to form a energy harvesting system preferably includes advanced, high charge piezoelectric ceramic fibers (PZT, PLZT, or other electro-chemistries), rods, foils, composites, or other shapes (hereinafter referred to as "piezoelectric ceramic fibers").

Piezoelectric ceramic fibers produced by the Viscose Suspension Spinning Process (VSSP) are one example of advanced, high charge piezoelectric ceramic fibers. VSSP is a relatively low-cost technology that can produce superior fibers ranging from about 10 microns to about 250 microns. Methods of producing ceramic fibers using VSSP are disclosed, for example, in U.S. Pat. No. 5,827,797 and U.S. Pat. No. 6,395,080, the disclosures of which are incorporated herein by reference in their entirety.

Figure 3:
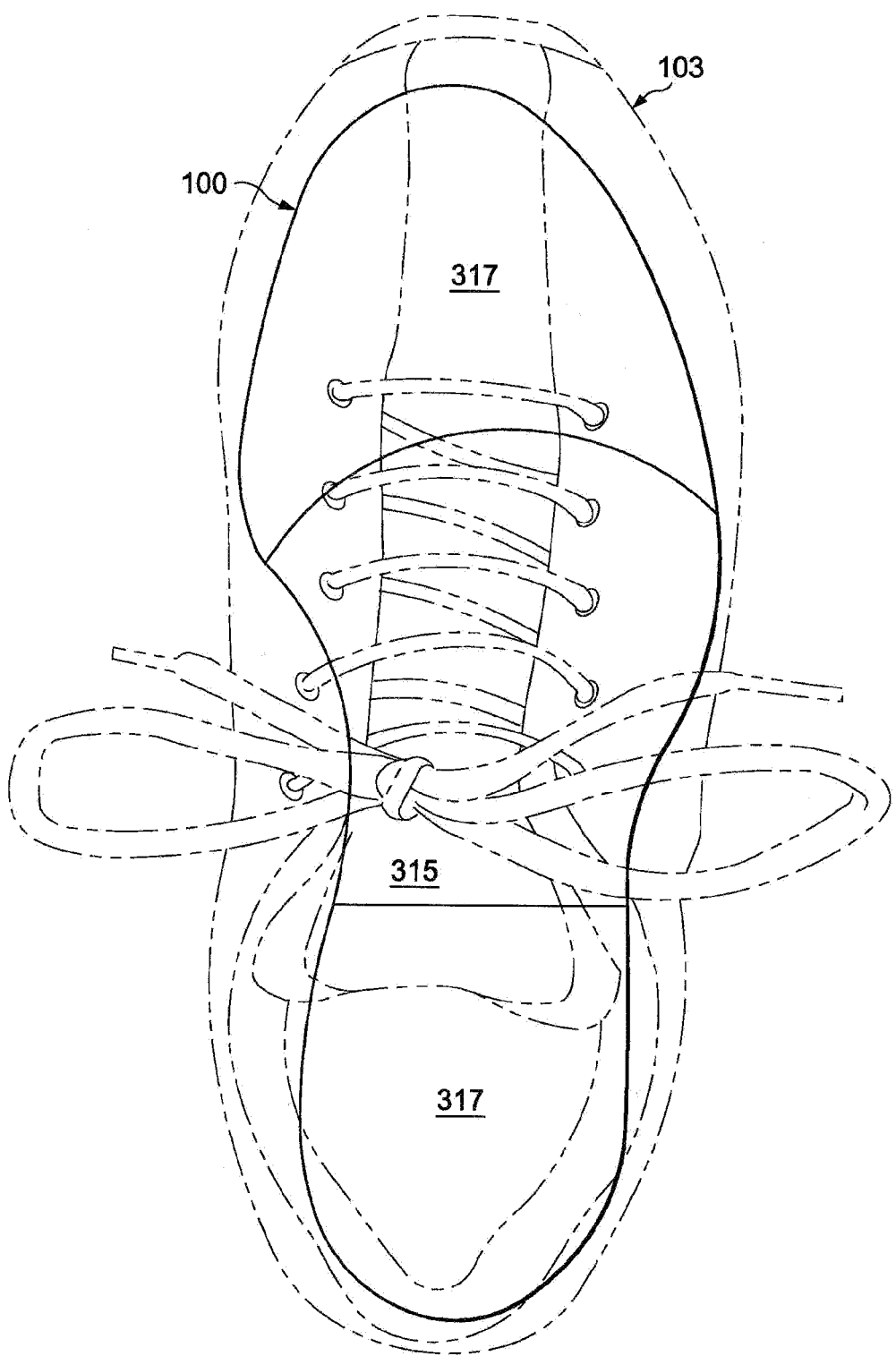
FIG. 3 illustrates a top view of the shoe insert and shoe of the present invention.

FIG. 1 illustrates one embodiment of a shoe insert 100 of the present invention. The physiotherapeutic shoe insert 100 may be positioned in the sole of the shoe in order to provide electrical stimulation of the cutaneous nerve endings. It substantially positioned in the bottom of the shoe allowing for the foot to be freely positioned within the shoe 103 (FIG. 3). The edges of the shoe insert 100 may extend along the side of the shoe 103.

Figure 2:
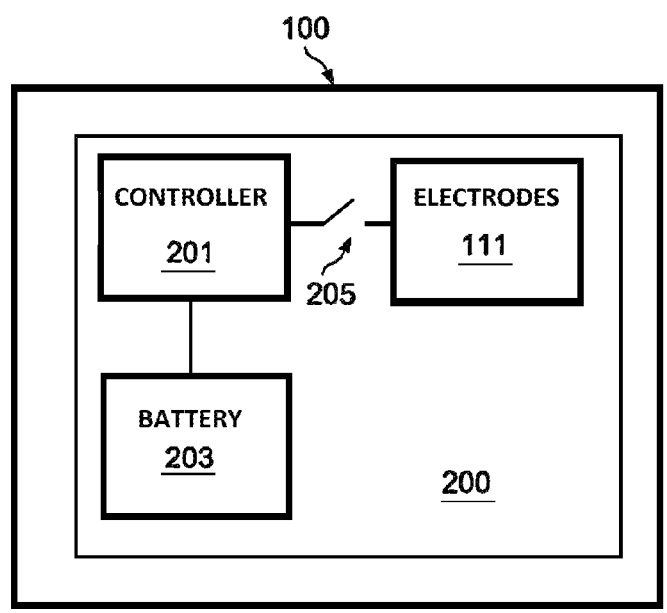
FIG. 2 illustrates a circuit diagram to be used in conjunction with the shoe insert of the present invention.

A pressure-activated conductive rubber may be used such as that described in U.S. Provisional Patent Application No. 60/646,265 filed Jan. 24, 2005, herein incorporated by reference in its entirety. In such an application, the physiotherapeutic shoe insert 100 may be formed form an appropriate pressure-activated conductive rubber (although other elastomers may be used). The shoe insert 100 may include a top surface 109, a bottom surface 105 and a periphery side surface 107. There are a plurality of conductive eyelet electrodes 111 distributed throughout the top surface 109, the bottom surface 105 and the side surface 107. The integrated electrodes 111 receive electrical impulses directly proportional with the pressure and/or time applied on the shoe insert 100. Thus, based on the movement of a user and the amount of movement, electrical impulses are applied. For example, increased movement will result in an increase in electrical therapy. This can be a highly advantageous result as it allows the therapy provided by the device to be self-regulating. In other embodiments, a controller 201 as shown in FIG. 2 may control the electrical impulses to be applied to the electrodes 111 or could be applied to the battery 203 for application at a later time. The controller 201 may direct the energy stored in the battery 203 to the electrodes 111 to apply the electrical impulses during periods of inactivity.

Figure 4:
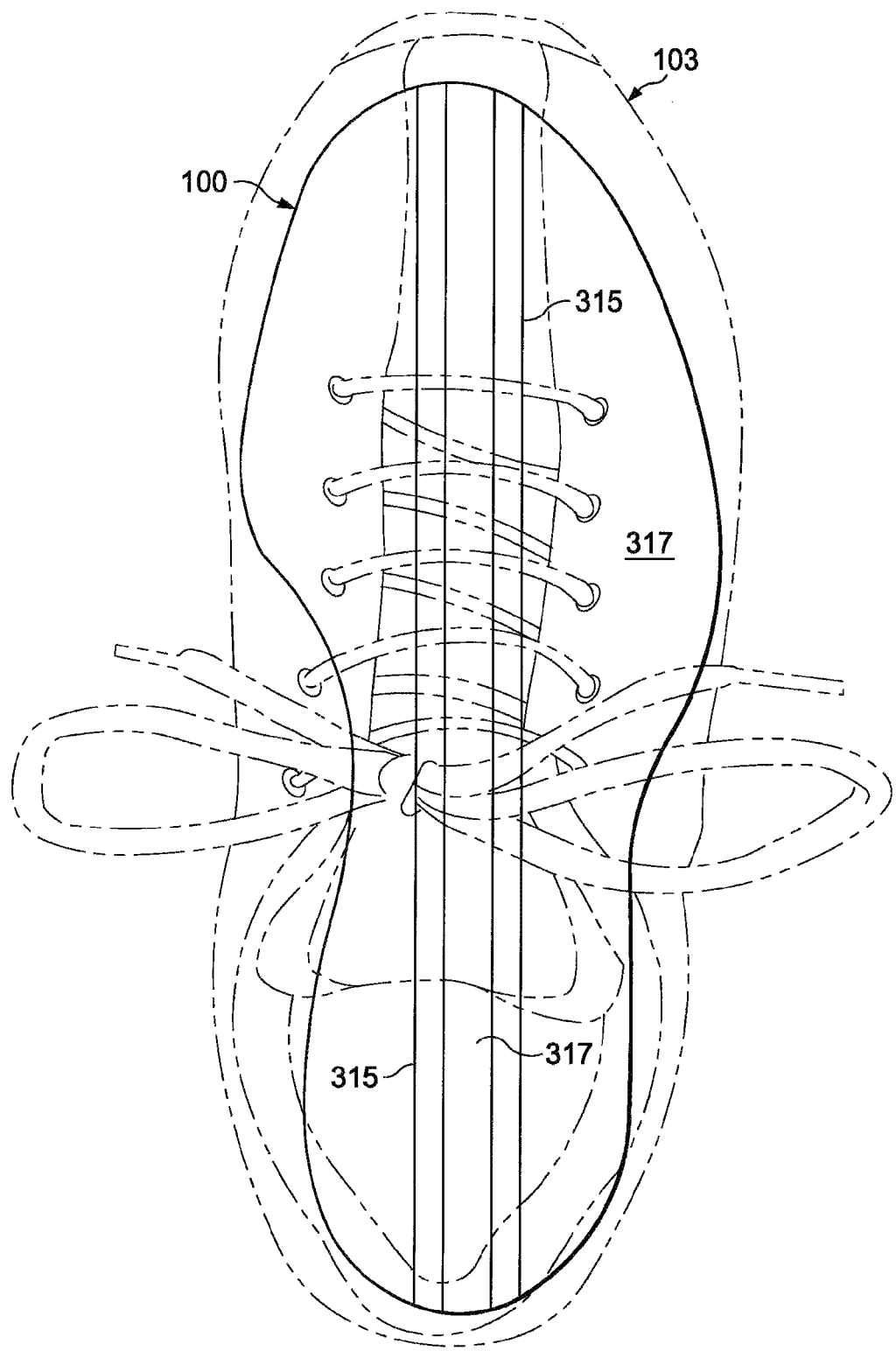
FIG. 4 illustrates an another top view of the shoe insert and shoe of the present invention.

FIG. 4 illustrates a top view of the shoe member 103 and the shoe insert 100 and illustrates conductive surface 315 and an insulating surface 317 of the shoe insert 100.

Figure 5:
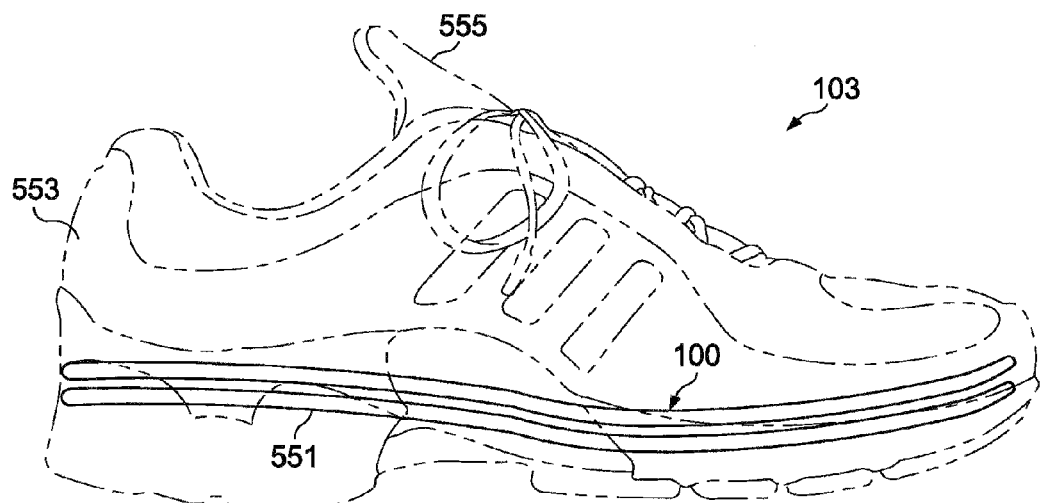
FIG. 5 illustrates a side view of the shoe and shoe insert.

FIG. 5 illustrates a side view of the shoe 103 and illustrates the side 553 of the shoe 103, the sole 551 of the shoe 103. FIG. 5 additionally illustrates a side view of the shoe insert 100 which is positioned over the sole 551 of the shoe 103 and illustrates the tongue 555 of the shoe 103.

Figure 6:
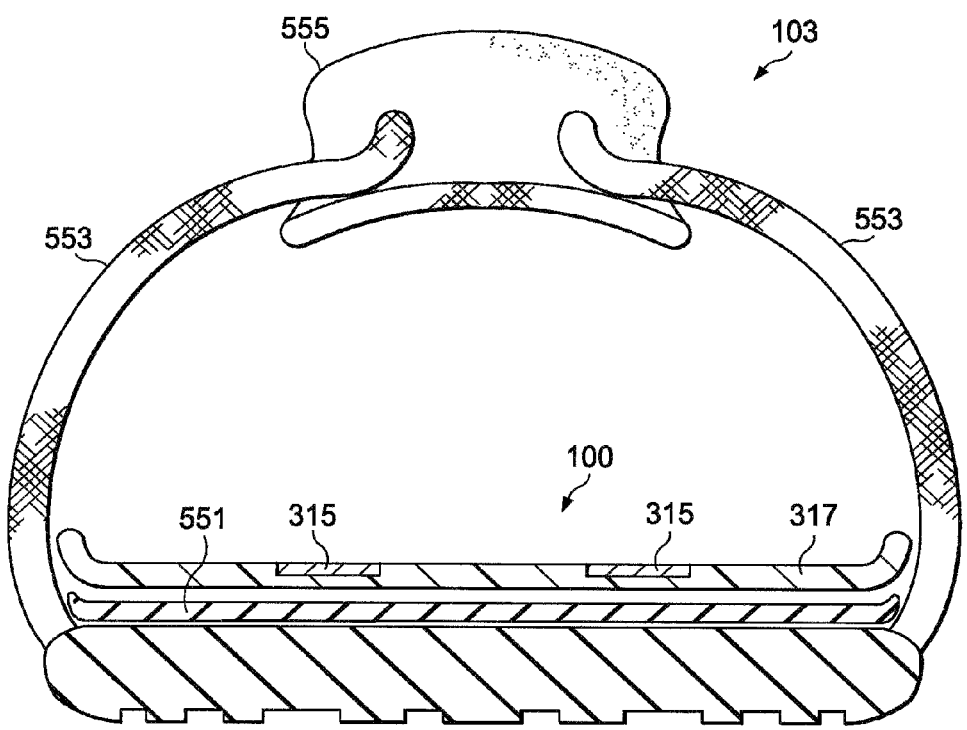
FIG. 6 illustrates a cross-sectional view of the shoe and shoe insert

FIG. 6 illustrates a cross-sectional front view of the shoe 103 and illustrates the side of 553 of the shoe 103, the sole 551 of the shoe 103. FIG. 5 additionally illustrates the shoe insert 100 which may be positioned over the sole 551 of the shoe 103 and illustrates the tongue 555 of the shoe and 103.

Note that the electrodes 111 or 315 can be positioned in any number of arrangements as may be appropriate for a particular treatment, or the electrodes can merely be positioned throughout the physiotherapeutic device 100.

The material used in the physiotherapeutic device or shoe insert 100 may be formed with an appropriate pressure-activated conductive rubber prepared through sonic homogenization. One method of forming an appropriate pressure-activated conductive rubber may be to sonically homogenize a mixture of an electroactive powder and a conductive rubber. One example of an appropriate conductive rubber is ZOFLEX ZL 60.1 pressure-activated conductive rubber. Ultrasound is applied to a mixture (such as a 1:1 mixture) of an electroactive powder such as a Terfernol-D ($Tb_3Dy_7F_e$) powder, or EC-65, EC-97 or EC-98 electroceramic powders. The ultrasound frequency can be 20 KHz. The mixture may be polarized through application of a DC voltage to produce a closed cell formation. The material can be further polarized under high compressed pressure. Instead of a conductive rubber, other types of conductive elastomers can be used.

Electroactive fibers may be embedded in a fabric-type material into the shoe insert 100. The shoe insert 100 may be formed integral with the shoe 103 and may include as illustrated at FIG. 3, it includes a plurality of PZT fibers or strips 315 integrated into the fabric longitudinally along the longitudinal direction of the shoe 103. By integrated it is meant operatively installed to the shoe. Some examples, not exclusive, are either physically incorporated into the fabric or material, or otherwise attached to the outer or inner surface of the material. While fibers or strips 315 might be removable, it is believed preferable to make them permanently integrated with the material.

In this example, fibers 315 are Piezoelectric Ceramic Fibers PZT and are incorporated as strips into the shoe insert material. Fibers 315 may be at least somewhat elastic or elastomeric, such that they bend and twist with movement of the foot within the shoe insert 100.

One example of fibers 315 are PZT fibers manufactured by Viscose Suspension Spinning Process (VSSP) method with cross-sections of 10 to 250 microns.

The fibers can be made in a form that is like other fabric threads. It therefore can be integrated into fabrics and materials of clothing, including but not limited to knee guards, elastic wraps, and other apparatus or clothing, by known manufacturing methods. The fibers are believed robust enough to take conventional manufacturing techniques for these types of materials without material damage to their function or efficacy. The fibers could replace normal fibers or be added to normal fibers or materials. They can be placed in just one portion of clothing, or in a plurality of positions. Different sets could be placed in different positions. It may be possible to have different sets of fibers in the same location.

The fibers could also be strips or other forms. They have electroactive or piezoelectric type properties. They output a voltage when subjected to some mechanical force.

A piezoelectric material may be defined as a material that develops an electric charge when pressed or subjected to a force. PE materials transform mechanical work input into electrical output and vice versa. A simple piezoelectric accelerometer consists of a disk-like base of PE material connected to a proof mass. The base is secured to the moving body and electrodes are connected on either side of the disk. When the body accelerates, the proof mass exerts a force on the PE disk and a charge builds up across the electrodes. Piezoelectric accelerometers are called active devices since they generate their own signals, and theoretically do not need to be powered.

The piezoelectric property of ceramics like PZT does not arise simply from its chemical composition. In addition to having the proper formulation, the piezoceramic must be subjected to a high electric field for a short period of time to force the randomly oriented micro-dipoles into alignment. This alignment by application of high voltage is called "poling". At a later time, if an electric field is applied in the opposite direction it exerts a "dislodging stress" on the micro-dipoles. Low level applied fields result in no permanent change in the polarization (it bounces back upon removal). Medium fields result in partial degradation of the polarization (with partial loss of properties). High applied fields result in repolarization in the opposite direction.

A conductive bond may be made between a metal substrate and the piezo part. Then one electrical lead is attached to the substrate, and one to the outward face of the piezoceramic sheet. In cases where a conductive bond is not possible (i.e. when the substrate is glass or plastic), a wire must be soldered to the "down" side of the ceramic at some location and a corresponding 'dish', 'cutout', or 'overhang' must be used to allow room for the wire when bonding the piezo sheet to the substrate.

Many piezoceramic parts come with a thin (.about.3000 Angstrom units) metallic electrode already on the ceramic. Wire leads can be soldered (use ordinary 60/40 resin core solder) anywhere on the electrode to suit the application/experiment. Most PSI ceramics have thin nickel electrodes and require the use of an additional liquid flux for uniform results.

In one example, fibers 315 could be operatively connected to an epoxy multilayer transducer which harvests or collects the electrical energy generated by fibers 315 and transfers the harvested electrical energy to an elongated elastic electrode that may be also integrated into shoe insert 100 along its length.

Therefore therapeutically application of electrical fields to the cutaneous nerve endings cutaneous nerve endings of the medial calcaneal branch of tibial nerve, medial plantar nerve, lateral plantar nerve, saphenous nerve, deep peroneal nerve, superficial peroneal nerve, sural nerve, but not limited to, is accomplished, not just between relatively small electrodes adhered to the leg, like with many TENS units.

The transducers can take different forms. The multilayer example could have four layers of epoxy transducers electrically connected to an elastic electrode.

The electrodes can be silicone strips that can be integrated into or on the inner or outer side of shoe insert 100.

Pressure, mechanical strain, or motion on fibers 315, usually by movement of the user by walking or running, may generate a protective elliptic electric field via electrodes 315 (e.g. elastic conductive silicon rubber members). With a manually (optionally wirelessly) operated electronic switch 205 incorporated, for example, into or on the shoe insert, the whole device can be activated or deactivated by the user whenever desired or the controller 201 may be programmed to administer the electric field. An electric field is always associated with the presence of electric charges. It fills the space around the charge and is the mechanism of interaction between charges. A test particle with small known charge (Q) placed near a charge concentration will experience an accelerating force (F) due to the field. The value of the electric field (E) at that location is the ratio F/Q (a vector).

Thus, as can be seen, when shoe insert 100 is worn and electrical energy generated in fibers 315, the user's knee would be substantially enveloped in electrical fields. As can be appreciated, the number of fields can be designed by the number and configuration of electrodes used. The PZT fibers with transducers and electrodes can be incorporated into at least a portion of shoe insert 100.

The walking or running motion that arises when the user moves his/her leg will generate an electric field into the affected or injured cutaneous nerve endings of the medial calcaneal branch of tibial nerve, medial plantar nerve, lateral plantar nerve, saphenous nerve, deep peroneal nerve, superficial peroneal nerve, sural nerve, but not limited to, similar to that applied by conventional electrotherapy pads, but more comprehensively and in a less cumbersome manner. The device eliminates the necessity of any additional source of energy (batteries or AC) and is fully portable during exercises.

The system of the present invention is less bulky than most existing therapeutic systems, does not require a battery, is less restrictive and cumbersome, and is believed to be less costly. It improves mobility and provides a self-contained, continuous renewable energy generating source. Nothing must be carried in the user's hands or strapped to a user's waist. In addition, the therapeutic system of the present invention can be self-regulating to provide an appropriate level of therapy. Further it is contemplated that the physiotherapeutic shoe insert 100 can be worn during physical activity, including during exercise or even during competitive sports.

Figure 7:
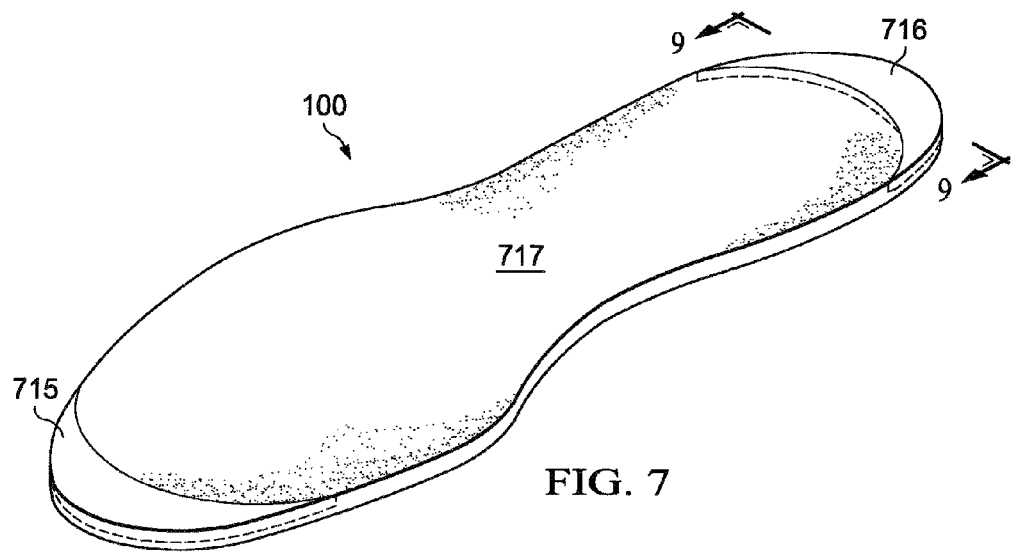
FIG. 7 illustrates a perspective view of another embodiment of the present invention.

FIG. 7 illustrates a perspective view of the shoe insert 100 and illustrates an insulating surface 717 being substantially coplanar with the first conductive surface 715 and a second conductive surface 716 of a first and second electrode 835, respectively. The first and second electrode 835 may only extend partially through the shoe insert 100.

Figure 8:
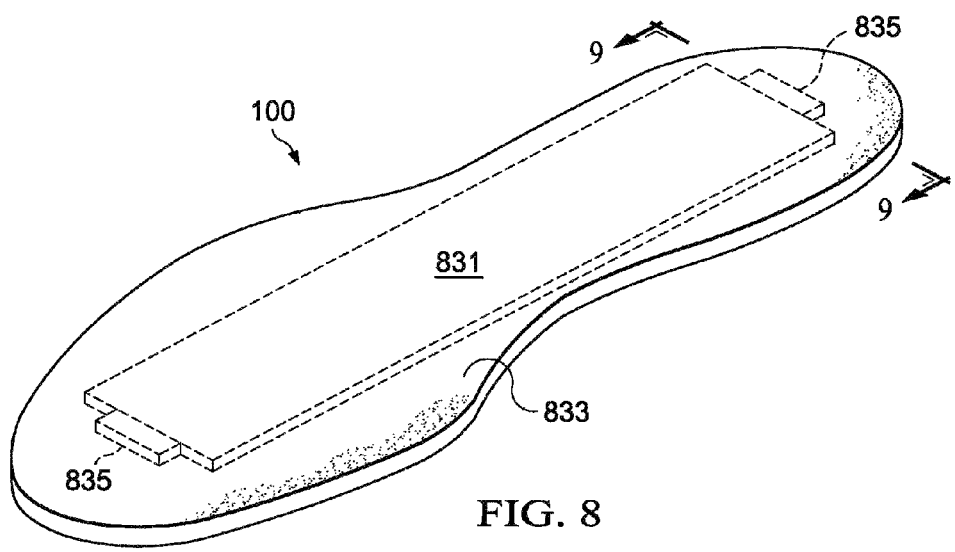
FIG. 8 illustrates a bottom view of another embodiment of the present invention depicted in FIG. 7.

FIG. 8 illustrates the shoe insert 100 which may include a piezoelectric member 831 which may be connected to electrodes 835 and may be positioned over or within an insulative surface 833.

Figure 9:
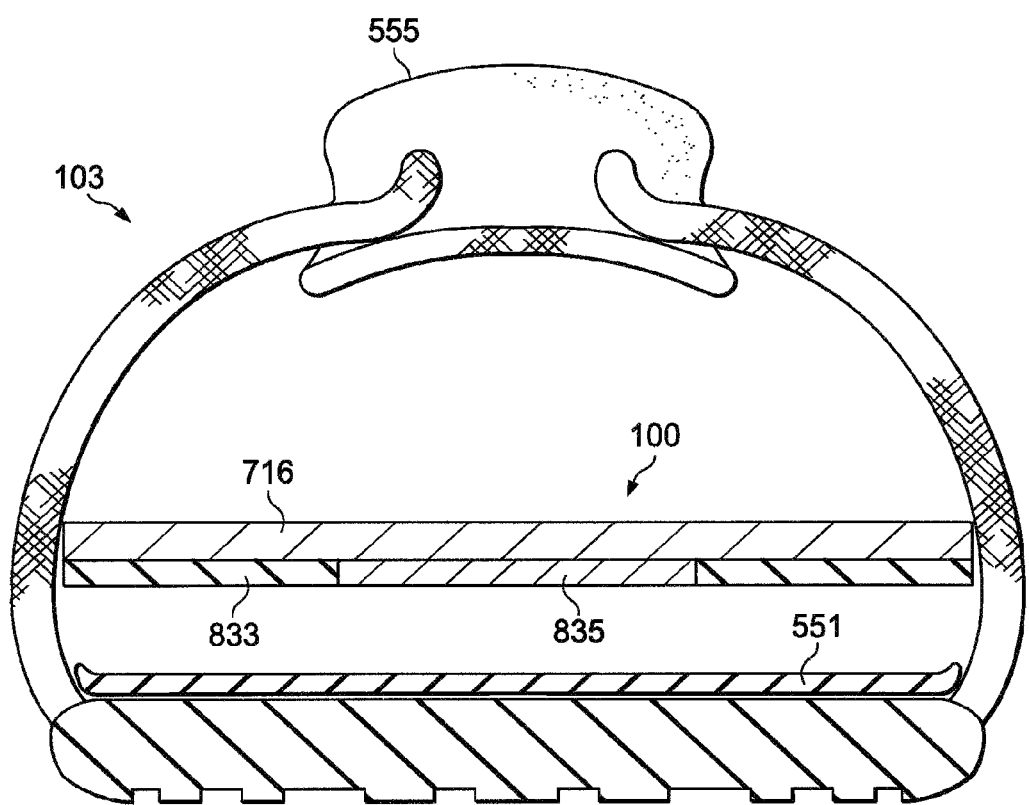
FIG. 9 illustrates a cross-sectional view of the embodiment of the present invention depicted in FIGS. 7 and 8.

FIG. 9 illustrates a cross-sectional view along section line 99 (from FIGS. 7 and 8) and illustrates that the electrode 835 extends partially across the shoe insert 100 which is positioned within the shoe 103.

Figure 10:
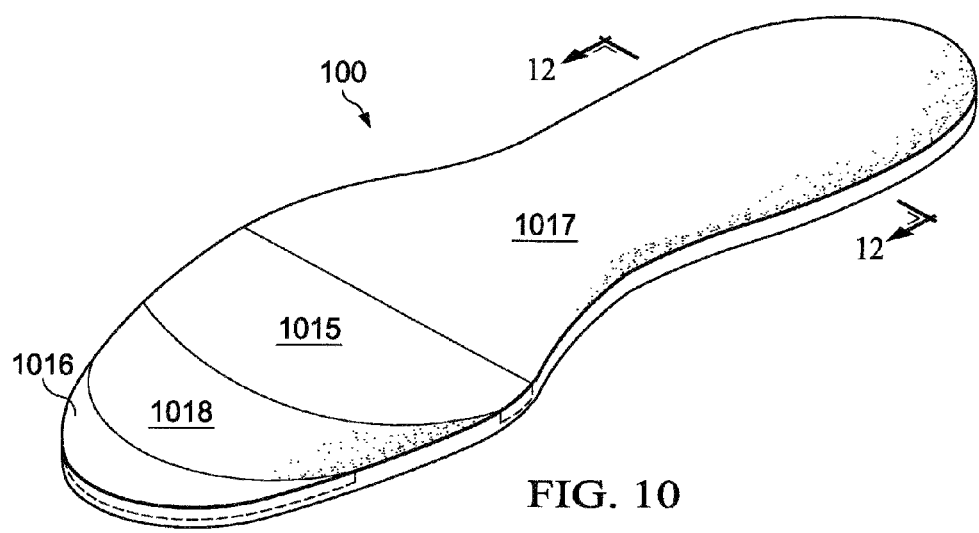
FIG. 10 illustrates a perspective view of another embodiment of the present invention.

FIG. 10 illustrates a perspective view of the shoe insert 100 of the present invention and illustrates a first insulating surface 1017 and a second insulating surface 1018 which may be positioned between a first conductive surface 1015 and a second conductive surface 1016. The first and second insulating surface 1017 and 1018 and the first and second conductive surface 1015 and 1016 may be substantially coplanar with the first and second insulating surface 1017 and 1018. The first and second conductive surface 1015 and 1016 may partially extend into the shoe insert 100.

Figure 11:
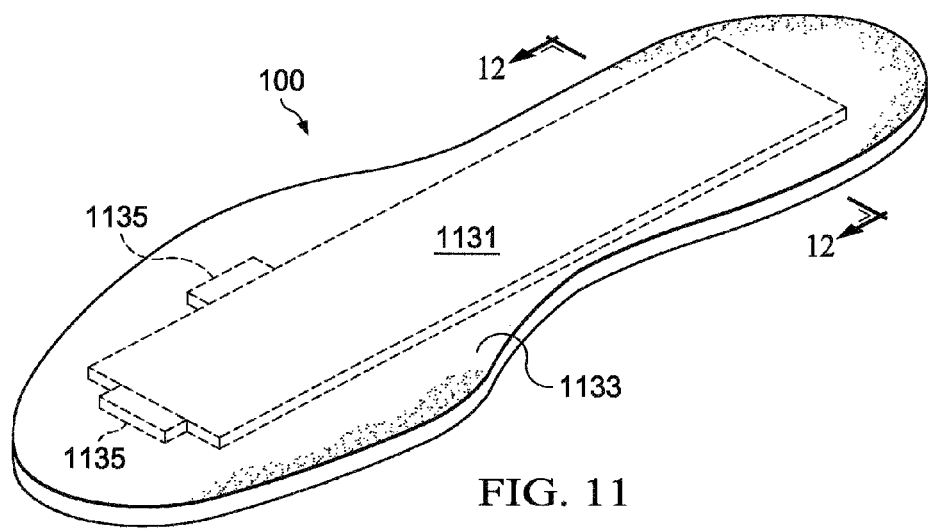
FIG. 11 illustrates a bottom view of another embodiment of the present invention depicted in FIG. 10.

FIG. 11 illustrates the shoe insert 100 which may include a piezoelectric member 1131 which may be connected to electrodes 1135 and may be positioned over or within an insulative surface 1133. One of the electrodes 1135 may be positioned along the end of the piezoelectric member 1131 with another of the electrodes 1135 may be positioned along the side of the piezoelectric member.

FIG. 12 illustrates the shoe insert 100 being positioned within the shoe 103 and above the insole 551 in a first and unstressed position where there may be little or no weight placed upon the shoe insert 100 by the user of the shoe 103.

Figure 13:
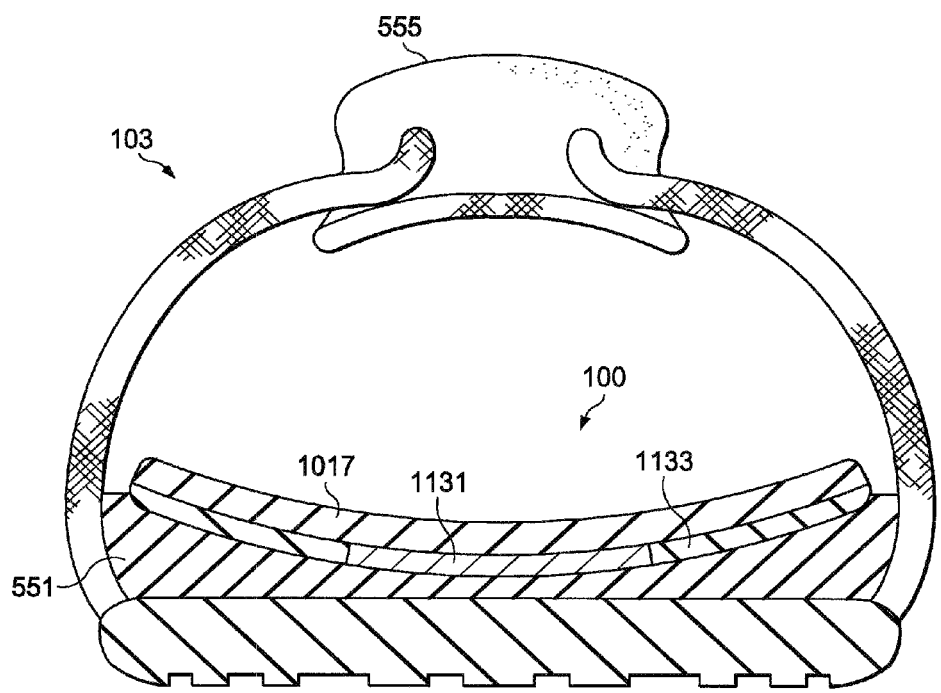
FIG. 13 illustrates a cross-sectional view of the shoe insert under load and in a second position.

FIG. 13 illustrates the shoe insert 100 being positioned within the shoe 103 and above the insole 551 in a second and stressed position where the weight of the user has been placed upon the shoe insert 100 by the user of the shoe 103.

Figure 14:
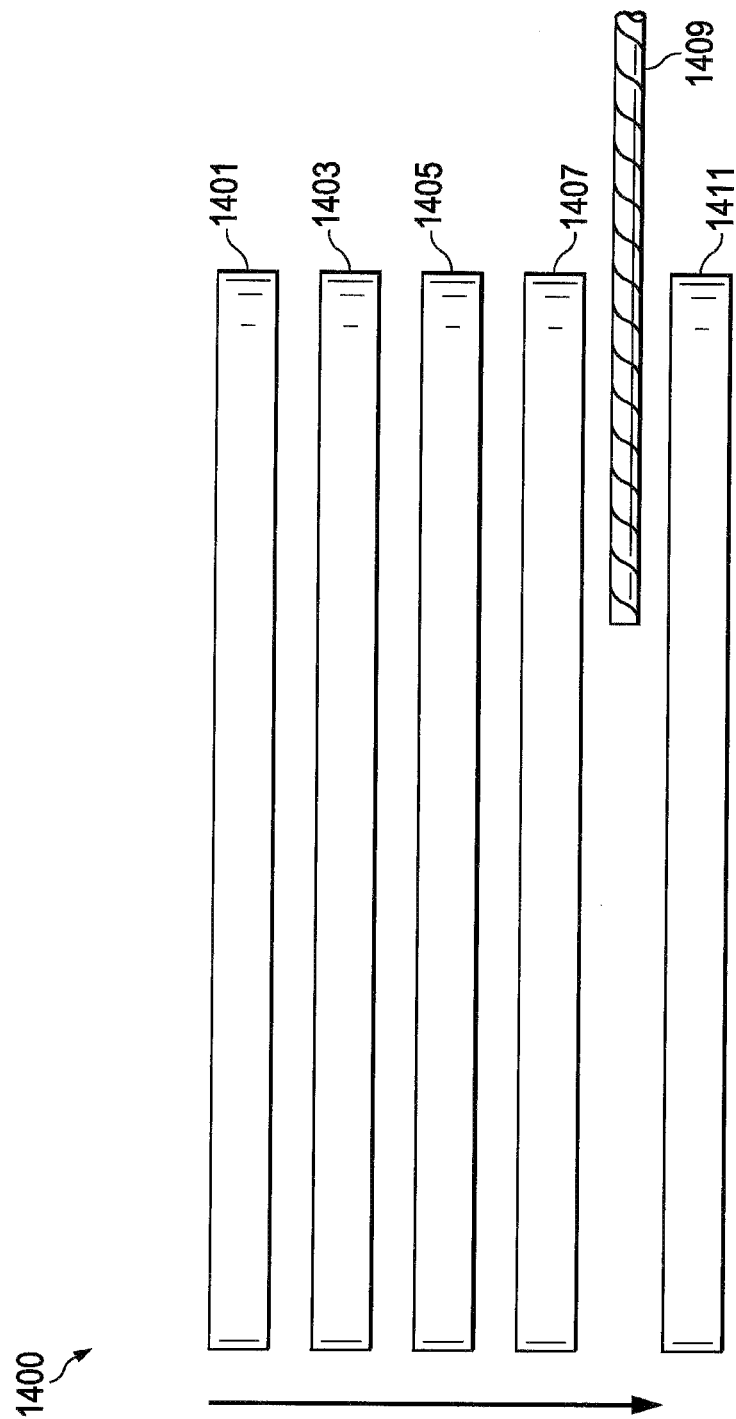
FIG. 14 illustrates an exploded view of an electrode of the present invention.
Figure 16:
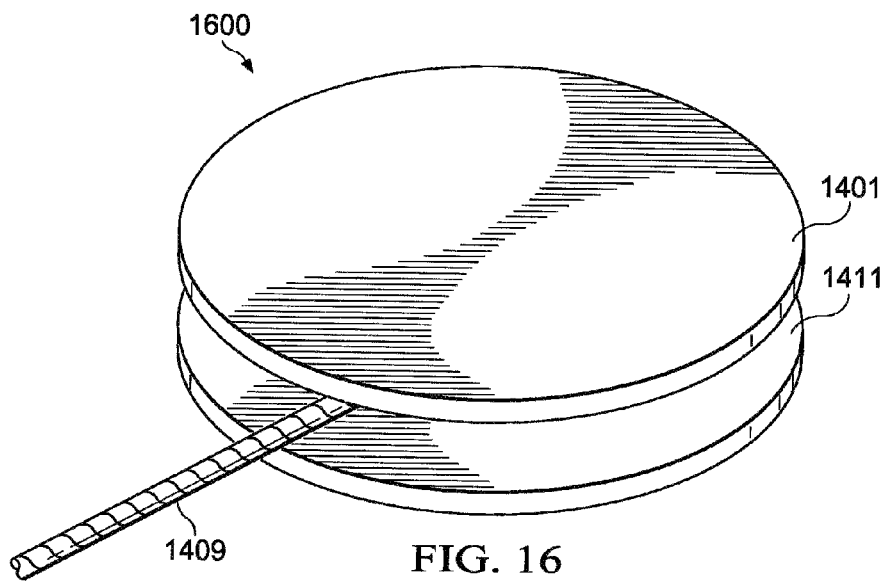
FIG. 16 illustrates a perspective view of another electrode of the present invention.
Figure 15:
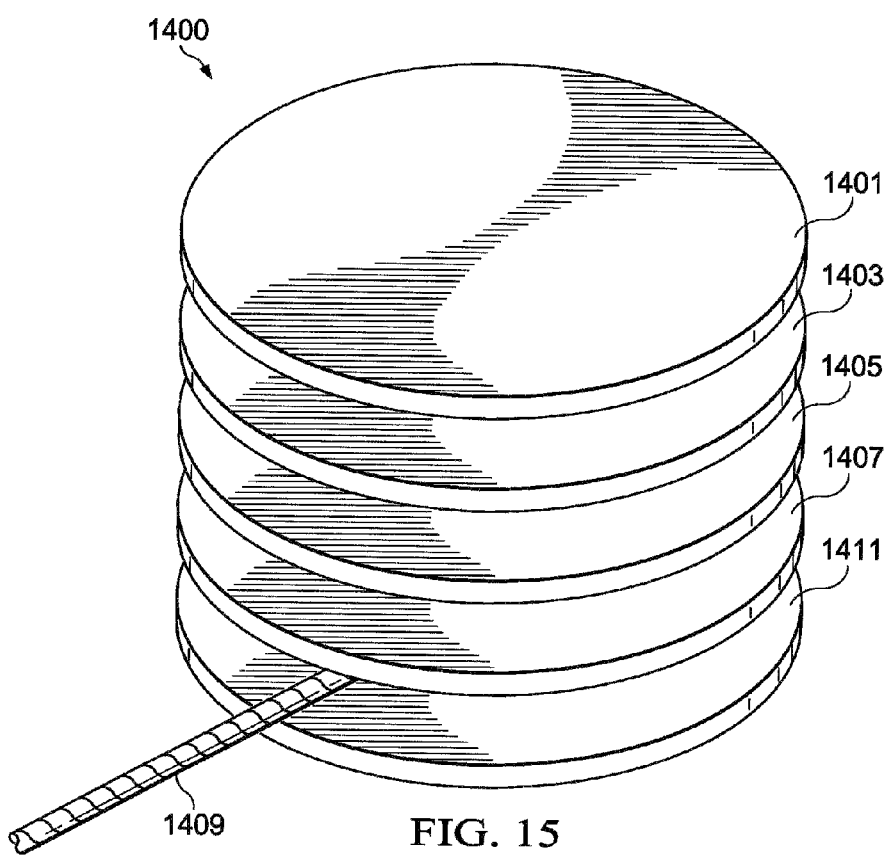
FIG. 15 illustrates a perspective view of the electrode of the present invention.

FIGS. 14, 15 and 16 illustrate electrodes 1400 and 1600, alternative to electrodes 111, 315, 835, and 1135, which may be used as an electrode as described above. The electrodes 1400 and 1600 may be a transcutaneous medical electrode for stimulating nerves and/or muscles by generating electricity that could be used in different parts of the body. The electrodes 1400 and 1600 may include a substantially dry body comfortable, electrically conductive interfacing layer of a metal-integral conductive silicon rubber sheet to be used where adhesive electrodes may not be appropriate or desirable. The electrically conductive interfacing layer of a metal-integral conductive silicon rubber sheet may be an alternative to the conductive surface 715, 716, 1015, and 1016 described above. The electrodes 1400 and 1600 may be used as described above with a shoe insert or to replace an adhesive electrode where allergic reaction may be possible. FIG. 14 illustrates the electrode 1400 which may include a upper and first sheet 1401 of metal integral conductive silicon rubber which may be a silver, silver plated copper, or conductive metal plated material filled silicon, a second layer 1403 which may be a conductive adhesive gel layer to adhere to the first sheet 1403, a third sheet 1405 of a conductive carbon film to adhere to the second layer 1403, a fourth sheet 1407 which may be a conductive metal sheet and the metal may be silver or other appropriate metals, a electrical lead 1409 to conduct electrical energy generated by the electrode 1409 and position between the fourth sheet 1407 and the fifths sheet 1411 which may be a dielectric/non-conducting flexible backing sheet.

FIG. 15 illustrates the elastomer electrode 1400 which may include a upper and first sheet 1401 of metal integral conductive silicon rubber which may be a silver, silver plated copper, or conductive metal plated material filled silicon, a second layer 1403 which may be a conductive adhesive gel layer to adhere to the first sheet 1403, a third sheet 1405 of a conductive carbon film to adhere to the second layer 1403, a fourth sheet 1407 which may be a conductive metal sheet and the metal may be silver or other appropriate metals, an electrical lead 1409 to conduct electrical energy generated by the electrode 1400 and position between the fourth sheet 1407 and the fifth sheet 1411 which may be a dielectric/non-conducting flexible backing sheet.

FIG. 16 illustrates the electrode 1600 which may include a upper and first sheet 1401 of metal integral conductive silicon rubber which may be a silver, silver plated copper, or conductive metal plated material filled silicon, an electrical lead 1409 to conduct electrical energy generated by the electrode 1400 and position between upper and first sheet 1401 and the second sheet 1411 which may be a dielectric/non-conducting flexible backing sheet.

The preceding description of exemplary embodiments is for illustrative purposes only, and not for limitation of the invention. Variations obvious to those skilled in the art are included with the claimed invention. Variations to the preceding embodiments, including changes in dimensions and configurations, structures, and specific methodology are possible. Also, optional features can be added to the basic configuration.

The invention claimed is:

1. An electrical stimulation apparatus, comprising:
   a shoe insert shaped to be inserted into a shoe;
   at least one piezoelectric member disposed in the shoe insert, the at least one piezoelectric member having an active and an inactive state, such that the piezoelectric member generates electrical energy when in the active state;
   at least one electrode disposed in the shoe insert, the at least one electrode electrically connected to the at least one piezoelectric member, such that when the at least one piezoelectric member sends electrical energy to the at least one electrode, the at least one electrode provides electrical stimulation to a user in contact with the at least one electrode; and
   the at least one electrode including a plurality of layers, with a first layer of the at least one electrode comprising a metal integral conductive silicon rubber material, with the first layer positioned most proximate to the user, and with a second layer of the at least one electrode positioned adjacent the first layer, the second layer comprising a conductive adhesive gel material.

2. The electrical stimulation apparatus as recited in claim 1, wherein the at least one electrode including a third layer positioned adjacent the second layer, with the second layer between the first and third layers, the third layer comprising a carbon film material.

3. The electrical stimulation apparatus as recited in claim 2, wherein the at least one electrode including a fourth layer positioned adjacent the third layer, with the third layer between the second and fourth layers, the fourth layer comprising a sheet of conductive metal.

4. The electrical stimulation apparatus as recited in claim 3, wherein the conductive metal of the fourth layer includes silver.

5. The electrical stimulation apparatus as recited in claim 3, wherein the at least one electrode including a fifth layer positioned adjacent the fourth layer, the fifth layer being positioned most distal the user, the fifth layer comprising a dielectric material.

6. The electrical stimulation apparatus as recited in claim 4, including a conductor positioned between the fourth and fifth layers of the at least one electrode, the conductor for delivering electrical energy to the at least one electrode.

7. The electrical stimulation apparatus as recited in claim 5, and further including a controller electrically connected to each of the at least one piezoelectric member and the at least one electrode, the controller for controlling the delivery of the electrical energy from the at least one piezoelectric member to the at least one electrode.

8. The electrical stimulation apparatus as recited in claim 6, and further including a rechargeable power source electrically connected to the controller, the rechargeable power source recharged by electrical energy from the at least one piezoelectric member.

9. The electrical stimulation apparatus as recited in claim 7, wherein the controller further controls the delivery of electrical energy to the at least one electrode from at least one of the rechargeable power source and the at least one piezoelectric member.

10. A shoe insert operable to provide electrical stimulation to a user, comprising:
    at least one piezoelectric member integrated with the shoe insert, the at least one piezoelectric member having an active and an inactive state, such that the piezoelectric member generates electrical energy when in the active state; and a plurality of electrodes integrated with the shoe insert, the plurality of electrodes electrically connected to the at least one piezoelectric member, such that when the at least one piezoelectric member sends electrical energy to the plurality of electrodes, the plurality of electrodes provide electrical stimulation to the user when in contact with the plurality of electrodes;

at least one of the plurality of electrodes each including a plurality of layers, with a first layer of the at least one electrode comprising a metal integral conductive silicon rubber material, with the first layer positioned most proximate to the user, and with a second layer positioned adjacent the first layer, the second layer comprising a conductive adhesive gel material;

a controller electrically connected to each of the at least one piezoelectric member and the plurality of electrodes;

a power source electrically connected to the controller, the power source operable to store electrical energy from the at least one piezoelectric member; and the controller for controlling the delivery of electrical energy to the plurality of electrodes from at least one of the power source and the at least one piezoelectric member.

11. The electrical stimulation apparatus as recited in claim 10, wherein the at least one electrode including a third layer positioned adjacent the second layer, with the second layer between the first and third layers, the third layer comprising a carbon film material.

12. The electrical stimulation apparatus as recited in claim 11, wherein the at least one electrode including a fourth layer positioned adjacent the third layer, with the third layer between the second and fourth layers, the fourth layer comprising a sheet of conductive metal.

13. The electrical stimulation apparatus as recited in claim 12, wherein the at least one electrode including a fifth layer positioned adjacent the fourth layer, the fifth layer being positioned most distal the user, the fifth layer comprising a dielectric material.

14. The electrical stimulation apparatus as recited in claim 13, including a conductor positioned between the fourth and fifth layers of the at least one electrode, the conductor for delivering electrical energy to the at least one electrode.

15. The electrical stimulation apparatus as recited in claim 14, wherein the conductive metal of the fourth layer includes silver.

16. The electrical stimulation apparatus as recited in claim 10, wherein the first layer of the at least one electrode includes silver metal.

17. The electrical stimulation apparatus as recited in claim 10, wherein the first layer of the at least one electrode includes silver plated copper.

18. The electrical stimulation apparatus as recited in claim 10, wherein the first layer of the at least one electrode includes conductive metal plated material filled silicon.

* * * * *